United States Patent
Hu

(10) Patent No.: US 10,319,555 B2
(45) Date of Patent: *Jun. 11, 2019

(54) X-RAY DEVICE

(71) Applicant: Luxbright AB, Göteborg (SE)

(72) Inventor: Qiu-Hong Hu, Göteborg (SE)

(73) Assignee: Luxbright AB, Gothenburg (SE)

( * ) Notice: Subject to any disclaimer, the term of this patent is extended or adjusted under 35 U.S.C. 154(b) by 120 days.

This patent is subject to a terminal disclaimer.

(21) Appl. No.: 15/117,872

(22) PCT Filed: Feb. 10, 2015

(86) PCT No.: PCT/EP2015/052788
§ 371 (c)(1),
(2) Date: Aug. 10, 2016

(87) PCT Pub. No.: WO2015/118177
PCT Pub. Date: Aug. 13, 2015

(65) Prior Publication Data
US 2017/0011880 A1    Jan. 12, 2017

Related U.S. Application Data

(60) Provisional application No. 61/937,677, filed on Feb. 10, 2014.

(51) Int. Cl.
*G01V 5/00* (2006.01)
*G01N 23/22* (2018.01)
(Continued)

(52) U.S. Cl.
CPC .......... *H01J 35/065* (2013.01); *G01N 23/046* (2013.01); *G01N 23/22* (2013.01);
(Continued)

(58) Field of Classification Search
CPC .......... A61B 6/00; A61B 6/40; A61B 6/4007; A61B 6/405; A61B 6/44; A61B 6/48;
(Continued)

(56) References Cited

U.S. PATENT DOCUMENTS 5,744,911 A * 4/1998 Kim .................. H01J 1/135
315/105
7,085,351 B2 * 8/2006 Lu .................. A61B 6/4488
315/169.3
(Continued)

FOREIGN PATENT DOCUMENTS

EP   0732720 A1 * 9/1996 .............. H01J 1/304
GB   2332089 A     6/1999
(Continued)

OTHER PUBLICATIONS

Chinese Office Action dated Sep. 25, 2017 in Application No. 201580019030X, title: An X-Ray Device (including translation).
(Continued)

*Primary Examiner* — Anastasia Midkiff
(74) *Attorney, Agent, or Firm* — Knobbe, Martens, Olson & Bear, LLP

(57) ABSTRACT

Example embodiments presented herein are directed towards an x-ray generating device. The device comprises at least one electron emitter(s) that has an electrically conductive substrate. The electrically conductive substrate comprises a coating of nanostructures. The device further comprises a heating element attached to each electrically conductive substrate. The device further comprises an electron receiving component configured to receive electrons emitted from the at least one electron emitter(s). The device also comprises an evacuated enclosure configured to house the at least one electron emitter(s), the heating element and the electron receiving component. The at least one electron emitter(s) is configured for Schottky emission when the
(Continued)

heating element is in an on-state and the at least one electron emitter(s) is negatively biased.

15 Claims, 7 Drawing Sheets

(51) Int. Cl.
*H01J 35/06* (2006.01)
*H01J 35/32* (2006.01)
*G01N 23/046* (2018.01)

(52) U.S. Cl.
CPC ....... *G01V 5/00* (2013.01); *H01J 2201/30488* (2013.01); *H01J 2201/30496* (2013.01)

(58) Field of Classification Search
CPC . A61B 6/485; H05G 1/00; H05G 1/02; H05G 1/08; H05G 1/085; H05G 1/30; H05G 1/32; H05G 1/34; H05G 1/46; H05G 1/56; H05G 1/70; H01J 19/00; H01J 19/02; H01J 19/04; H01J 19/06; H01J 19/062; H01J 19/064; H01J 19/066; H01J 19/068; H01J 19/08; H01J 19/42; H01J 19/44; H01J 19/48; H01J 19/78; H01J 29/00; H01J 29/006; H01J 29/02; H01J 29/025; H01J 29/04; H01J 35/00; H01J 35/02; H01J 35/025; H01J 35/04; H01J 35/045; H01J 35/06; H01J 35/065; H01J 35/08; H01J 35/14; H01J 2201/00; H01J 2201/19; H01J 2201/196; H01J 2201/28; H01J 2201/30; H01J 2201/304; H01J 2201/30446; H01J 2201/30449; H01J 2201/30453; H01J 2201/30469; H01J 2201/3048; H01J 2201/30403; H01J 2201/30426; H01J 2201/30434; H01J 2201/30484; H01J 2201/30488; H01J 2201/30492; H01J 2201/30496; H01J 2201/306; H01J 2201/312; H01J 2201/3125; H01J 2201/319; H01J 2237/00; H01J 2237/02; H01J 2237/03; H01J 2237/032; H01J 2237/036; H01J 2237/038; H01J 2235/00; H01J 2235/02; H01J 2235/06
See application file for complete search history.

(56) References Cited

U.S. PATENT DOCUMENTS

| | | | |
|---|---|---|---|
| 7,850,941 B2* | 12/2010 | Tsakalakos | ............ C30B 11/12 |
| | | | 423/445 R |
| 2001/0019601 A1 | 9/2001 | Tkahashi et al. | |
| 2002/0094064 A1 | 7/2002 | Zhou et al. | |
| 2003/0036332 A1 | 2/2003 | Talin et al. | |
| 2004/0150311 A1 | 8/2004 | Jin | |
| 2005/0269528 A1* | 12/2005 | Kruit | ................... B82Y 10/00 |
| | | | 250/492.22 |
| 2011/0116603 A1 | 5/2011 | Kim et al. | |

FOREIGN PATENT DOCUMENTS

| | | |
|---|---|---|
| JP | 2001-250496 A | 9/2001 |
| JP | 2003-036805 A | 2/2003 |
| JP | 2005-332735 A | 12/2005 |
| JP | 2009-205992 A | 9/2009 |
| JP | 2012-033411 A | 2/2012 |
| JP | 2013-524452 A | 6/2013 |
| WO | 2011/124555 A1 | 10/2011 |

OTHER PUBLICATIONS

Chinese Office Action for Application No. 201580019030.X dated May 21, 2018 in 5 pages.
Office Action for Japanese Application No. 2016-568131, dated Jan. 11, 2019, in 26 pages (translation included).
Office Action for Japanese Application No. 2016-568131, dated Apr. 1, 2019, in 5 pages (translation included).

* cited by examiner

X-RAY DEVICE

CROSS-REFERENCE TO RELATED APPLICATIONS

This application is the U.S. National Phase under 35. U.S.C. § 371 of International Application PCT/EP2015/052788, filed Feb. 10, 2015, which claims the benefit of U.S. Provisional Application No. 61/937,677, filed Feb. 10, 2014. The disclosures of the above-described applications are hereby incorporated by reference in their entirety.

TECHNICAL FIELD

Example embodiments presented herein are directed towards an x-ray device that is configured to operate in Schottky emission mode.

BACKGROUND

X-rays are generated by the bombardment of energetic electrons on a metal surface. In this setting, an x-ray source is a device comprising an electron emitter known as the cathode and an electron receiver known as the target or anode. The anode is the x-ray emitter. The cathode and the anode are arranged in a particular configuration, and are enclosed in a vacuum housing. Moreover, an x-ray system may comprise the following components: the x-ray source, the computerized manipulation and handling device, the detectors, and the power unit(s). Moreover, in combination with other technology areas, x-ray finds applications in medical imaging, security inspection, and nondestructive testing in industry. Computer technology has revolutionized the use of x-ray in modern society, for example, x-ray CT scanner (computed tomography). The advancement in detector technology allowed improved energy resolution, digital images and continuously increasing scan areas. However, the technology for generating x-ray has essentially been the same since the birth of the Coolidge tube for about 100 years ago, when William Coolidge revolutionized the way x-ray were generated by replacing the gas-filled tubes with an evacuated tube, housing a hot tungsten filament to utilize thermionic emission.

SUMMARY

Perhaps all x-ray tubes used in x-ray imaging utilize hot cathodes of tungsten filaments based on thermionic emission. In the past decade or so, attempts were made to use carbon nanotubes (CNTs) as a cold cathode to generate X-rays by means of field emission. Such electron emission is induced by a high electric field without heating. CNTs are thought of as an ideal emitter of electrons. However, when using them in x-ray sources, the manufacturing process and work conditions seem to present severe challenges to their material properties. The current output is still well below the level for practical applications. Thus, at least one object of the example embodiments presented herein is to provide an alternative electron emitter, which may provide for alternate means of electron emission to overcome the material and operational disadvantages inherent in the hot cathodes, as well as in the cold cathodes based on CNTs; consequently and at the same time brings in improved performance of the X-ray sources. Furthermore, the example embodiments presented herein may provide for a portable X-ray device.

Thus, the example embodiments presented herein are directed towards an x-ray device that utilizes a hybrid emission, i.e. field emission or thermally assisted electron emission. More importantly, the example embodiments presented herein utilize a Schottky emission. The use of a thermally assisted electron emission allows for compensation in the properties of the hot and cold cathodes. The benefit of the example embodiments will be clear when comparisons are made between the Schottky emission, the thermionic emission, and the field emission. It is well known that a cold cathode can be poisoned by the adsorption of electronegative elements, such as S and Cl, existing as residual gaseous species in the tube. If the adsorption is severe, the cathode will cease to emit electrons. For a field emission X-ray tube, the cold cathode can be regenerated by removing the tube from the housing and baking out the entire tube in an oven, and then mount the tube back to see the effect of baking out—a cumbersome process. On the other hand, for a Schottky emission tube, the heating resulting in a moderate temperature rise at the cathode assists the emission of the electrons while at the same time preventing the adsorption of the poisoning gas atoms or molecules on the cathode. In case the poisoning occurs, the regeneration can be done by heating the cathode directly without removing the tube from the tube housing. The lower power consumption will result in a more compact power source to be utilized, thereby allowing for the x-ray device to become more portable. Furthermore, the use of such electron emission mode eliminates the need for a cooling system or long cool down and warm up periods that are common for hot filament-based systems.

The example embodiments presented herein are directed towards an x-ray generating device comprising at least one electron emitter(s) comprising an electrically conductive substrate. The electrically conductive substrate comprises a coating of nanostructures. The x-ray device further comprises a heating element attached to each electrically conductive substrate of the at least one electron emitter(s). The x-ray device further comprises an electron receiving component configured to receive electrons emitted from the at least one electron emitter(s). The x-ray device further comprises an evacuated enclosure configured to house the at least one electron emitter(s), the heating element and the electron receiving component. The at least one electron emitter(s) is configured for Schottky emission when the heating element is in an on-state and the at least one electron emitter(s) is negatively biased.

An example advantage of the above embodiment is the elimination of a cooling system or long cool down and warm up periods that are common for hot filament-based systems that utilize thermionic emission. Thus, a more portable x-ray device may be obtained.

According to some of the example embodiments, the at least one electron emitter(s) is further configured for field emission when the heating element is in an off-state and the at least one electron generating component(s) is negatively biased.

Thus, according to such example embodiments, the x-ray device may be configured for dual operational modes allowing for both field emission and Schottky based emission. Such an embodiment has the example advantage of providing a versatile device that may provide x-ray images at various resolutions and contrast levels.

According to some of the example embodiments, the x-ray device may further comprise an electrical power source configured to control an operational state of the heating element.

The electrical power source may, for example, control the electron emission from the at least one electron emitter(s).

Furthermore, according to the example embodiments in which the at least one electron emitter(s) comprises a plurality of electron emitters, the power source may be used to selectively activate the different electron emitters. Such an embodiment has the example advantage of providing a more versatile device in which the separate components of the device may be individually controlled.

According to some of the example embodiments, the electrical power source 28 is further configured to supply a potential difference between the at least one electron generating component(s) and the electron receiving component for a diode tube in three bias modes, (−,0: cathode negative, anode grounded), (−,+: cathode negative, anode positive) and (0,+: cathode grounded, anode positive). The use of such bias modes is provided for inducing the Schottky emission or field emission.

Thus, an example advantage of such an embodiment is the elimination of a cooling system or long cool down and warm up periods that are common for hot filament-based systems that utilize field emission. Thus, a more portable x-ray device may be obtained.

According to some of the example embodiments, the electrical power source is configured to operate in DC mode, i.e. constant (−, 0), (−, +), (0, +); pulse mode, i.e. square waves with Vp>0 at the anode or Vp<0 at the cathode; or AC mode, i.e. a sinus wave.

An example advantage of providing an electrical power source with different modes of operation is the ability of providing a more versatile device. For example, in pulse and AC modes, a defined rising time, frequency, duty cycle and pulse shape of waveform may be obtained.

According to some of the example embodiments, the electrically conductive substrate is made of stainless steel, nickel, nickel based alloys, iron or iron based alloys.

According to some of the example embodiments, the nanostructures are doped or co-doped with a dopant element from column IA, IIA, IB, IIIA, VIA, or VIIA in the periodic table of elements.

According to some of the example embodiments, the nanostructures are made of ZnO.

An example advantage of such embodiments is the ability of providing an alternative to the CNT based electron emitters. The use of such an alternative provides an example benefit of providing an electron emitter that is more compatible with Schottky based emission. Carbon based electron emitters are prone to damage at the temperatures and reactive gaseous environment of a typical tube manufacturing process, whereas ZnO and related materials are high in melting temperature and chemically more stable with equally attractive field emission performance to CNTs.

According to some of the example embodiments, the electron-receiving component is made of metal, a metallic alloy, a metallic compound, or a metal ceramic composite.

Some of the example embodiments are directed towards the use of the x-ray generating device described above, in a security x-ray scanning apparatus.

Some of the example embodiments are directed towards the use of the x-ray generating device described above, in a computed tomography scanning apparatus.

Some of the example embodiments are directed towards the use of the x-ray generating device described above, in a C-arm type scanning apparatus.

Some of the example embodiments are directed towards the use of the x-ray generating device described above, in a geological surveying apparatus.

Some of the example embodiments are directed towards the use of the x-ray generating device described above, in X-ray fluorescence spectrometry.

BRIEF DESCRIPTION OF THE DRAWINGS

The foregoing will be apparent from the following more particular description of the example embodiments, as illustrated in the accompanying drawings in which like reference characters refer to the same parts throughout the different views. The drawings are not necessarily to scale, emphasis instead being placed upon illustrating the example embodiments.

DETAILED DESCRIPTION

In the following description, for purposes of explanation and not limitation, specific details are set forth, such as particular components, elements, techniques, etc. in order to provide a thorough understanding of the example embodiments. However, it will be apparent to one skilled in the art that the example embodiments may be practiced in other manners that depart from these specific details. In other instances, detailed descriptions of well-known methods and elements are omitted so as not to obscure the description of the example embodiments. The terminology used herein is for the purpose of describing the example embodiments and is not intended to limit the embodiments presented herein.

Figure 1:
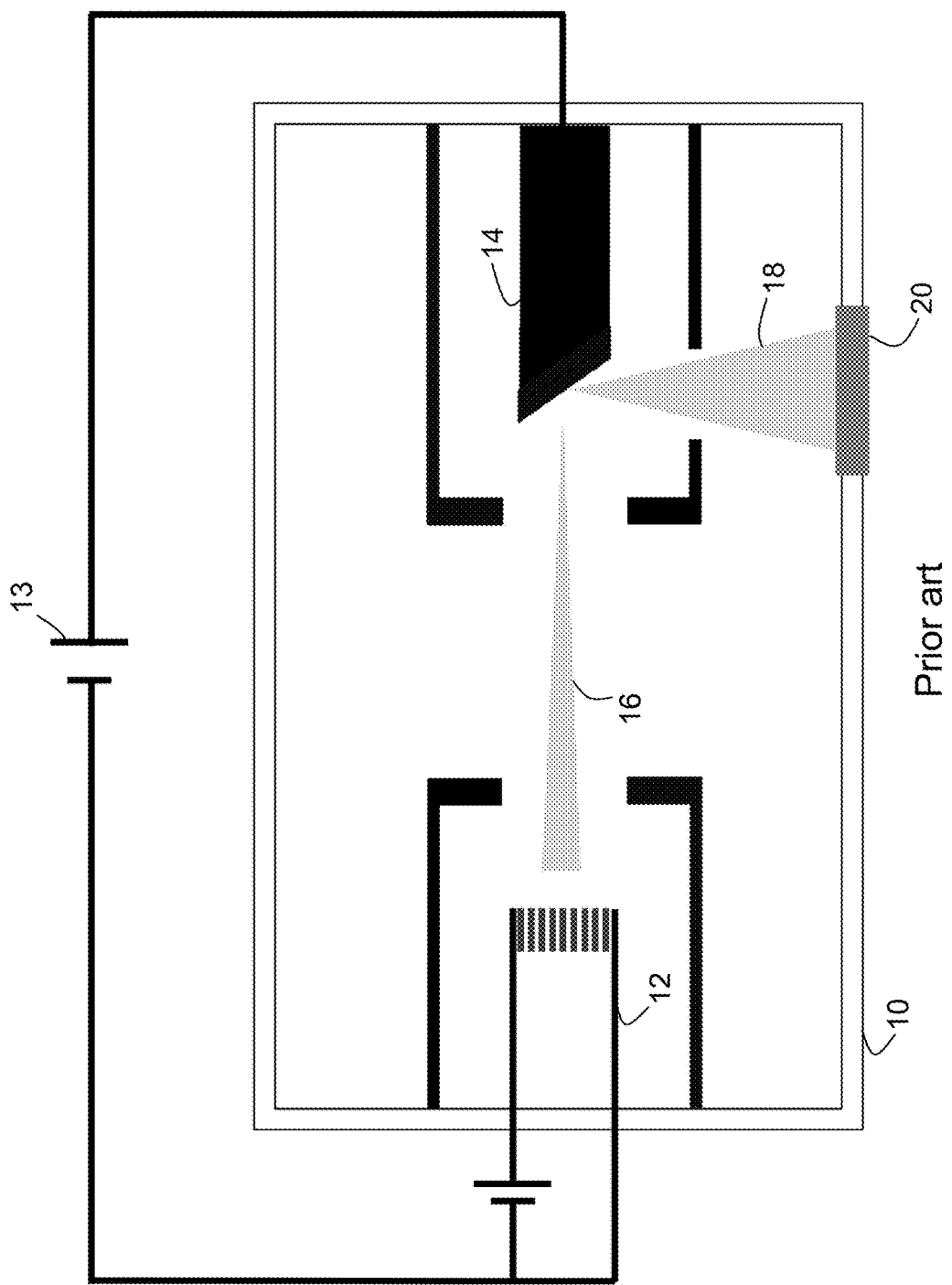
FIG. 1 is a schematic of an x-ray device based on thermionic emission.

Example embodiments presented herein are directed towards an x-ray device that utilizes Schottky based electron emission. In order to better describe the example embodiments, a problem will first be identified and discussed. FIG. 1 illustrates a traditional x-ray tube. The x-ray tube of FIG. 1 features an evacuated glass tube 10 comprising a hot filament cathode 12 and an anode 14 made of refractory metal/alloy. The surface of the anode 14 faces the cathode 12 at a predetermined inclination angle. An electric current, provided by a power supply 13, passes through the filament cathode 12 causing an increase in the temperature of the filament 12 to a level that emits an electron beam 16 from this filament. The electrons in the electron beam 16 are then accelerated towards the anode 14 with an electric field. This results in an x-ray beam 18 that is directed out of the device via a window 20. The voltage difference between the cathode and the anode determines the energy of the x-ray beam.

Perhaps all x-ray tubes used in x-ray imaging utilizes hot cathodes of tungsten filaments based on thermionic emission. In the past decade or so, attempts were made to use carbon nanotubes (CNTs) as a cold cathode to generate X-rays by means of field emission. Such electron emission of is induced by a high electric field without heating. CNTs are thought as an ideal emitter. However, to use them in x-ray sources, the manufacturing process and work conditions seem to present severe challenges to their material properties. The current output is still well below the level for practical applications. Thus, at least one object of the example embodiments presented herein is to provide portable X-ray sources with improved performance due to an alternative electron emitter, which may provide for alternate means of electron emission to overcome the material and operational disadvantages inherent in the hot cathodes as well as in the cold cathodes based on CNTs. Thus, the example embodiments presented herein are directed towards an x-ray device which utilizes a hybrid emission, field emission or thermally assisted emission—Schottky emission. Specifically, the example embodiments presented herein utilize a Schottky based electron emission. The lower power consumption resulted from the hybrid emission will allow for a more compact power source to be utilized, thereby allowing for the x-ray device to become more portable. Furthermore, the use of such electron emission mode eliminates the need for a cooling system or long cool down and warm up periods that are common for hot filament-based systems.

Figure 2:
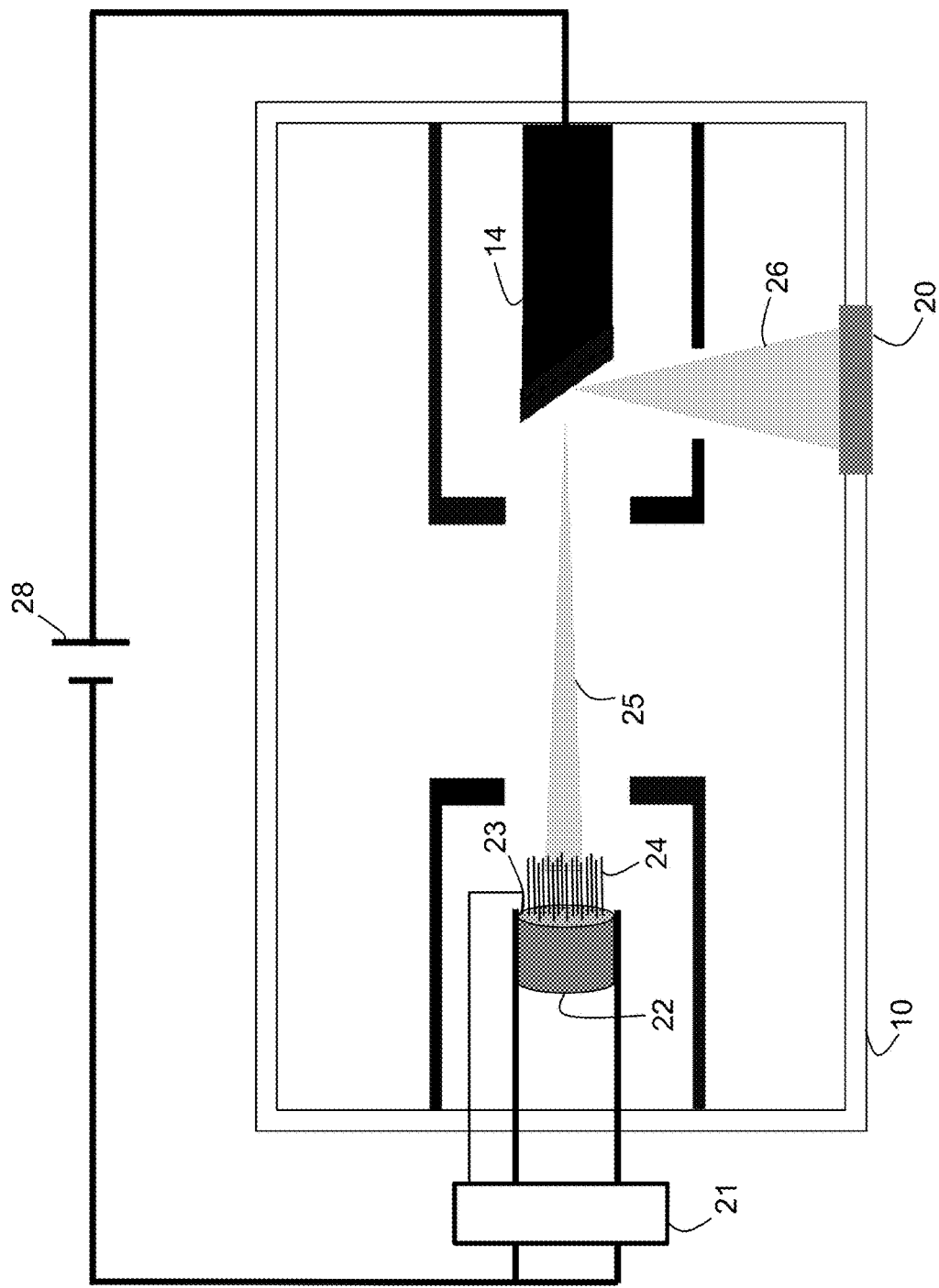
FIG. 2 is a schematic of an x-ray, according to the example embodiments described herein.

FIG. 2 illustrates an x-ray device according to the example embodiments. The x-ray device of FIG. 2 comprises an evacuated glass tube 10 comprising an electron emitter, or cathode, 22 and an electron-receiving component 14. The surface of the electron-receiving component 14 faces the electron emitter 22 at a predetermined inclination angle. An electric current, provided by a power supply 28, passes through a heating element 21 causing an increase in the temperature of the electron emitter 22 to a level that emits an electron beam 25 from the electron emitter 22. Such emission is known as Schottky emission. In contrast to the electron emission of FIG. 1, which is induced with the use of an electrostatic field, the emission of FIG. 2 is induced via thermal heating.

The electrons in the electron beam 25 are then accelerated towards the electron-receiving component 14 with an electric field. This results in an x-ray beam 26 that is directed out of the device via a window 20. The voltage difference between the electron emitter or cathode and the electron receiving component or anode determines the energy of the x-ray beam.

The electron emitter 22 comprises an electrically conductive substrate 23 comprising of a coating of nanostructures 24. The heating element 21 is attached to the electrically conductive substrate 23 via two electric feed-throughs at the cathode end of the tube. The nanostructure coating 24 may be grown on the electrically conductive substrate 23. The nanostructure coating may be in the form of nanoparticles, nanowires, nanorods, nano tetrapods or nanotubes. The materials of the substrate can be stainless steel, nickel, nickel-based alloys, iron or iron-based alloys. According to some of the example embodiments, the substrate is preformed into various shapes.

Figure 3:
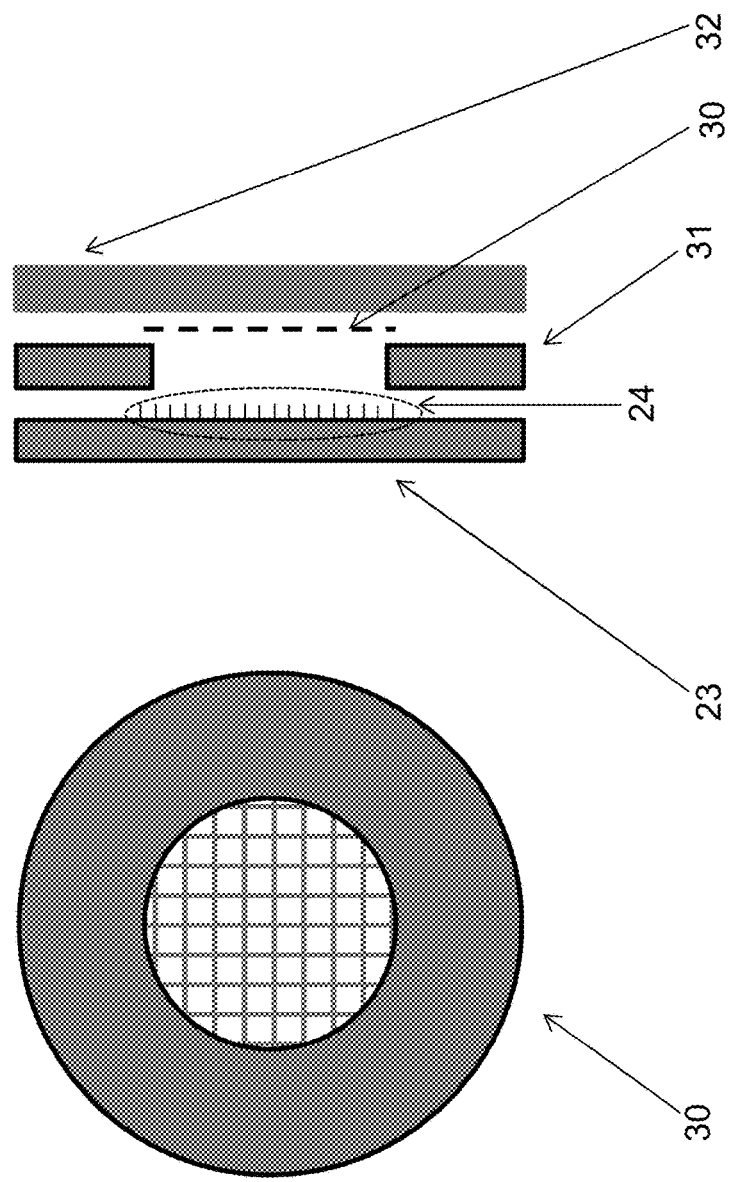
FIG. 3 is an illustrative example of an electron emitter with a grid, according to some of the example embodiments described herein.

According to some of the example embodiments, a grid 30 is placed in between the surface 23 comprising the nanostructures 24 of electron emitter and the electron-receiving component 14 that acts as an extraction electrode, as illustrated in FIG. 3. According to some of the example embodiments, a spacer 31 is placed between the electron emitter and the grid 30. The grid may be placed at an interval distance between 100 μm and 1000 μm to the electron emitter that is fixed via the spacer. A circular cover is placed on top of the grid acting as the grid electrode providing a voltage to the grid, 32. According to some of the example embodiments, the spacer may be a ceramic spacer.

The grid is made of electrically conductive wires of equal diameter. Furthermore, the wires are made of high melting point, low vapor pressure and electrically conductive materials, such as W, Mo, Ta, Ni, stainless steel, or nickel based alloys. The diameter of the wires varies between 30 μm and 150 μm. The opening ratio of the grid varies between 50% and 80%. Furthermore, the surface of the wires in the grid is coated with a thin layer or multilayers of material(s) with properties of pronounced secondary electron emission, such as MgO and related materials. Alternatively, the coating is a UV emitting material, GaN and related materials.

Figure 5:
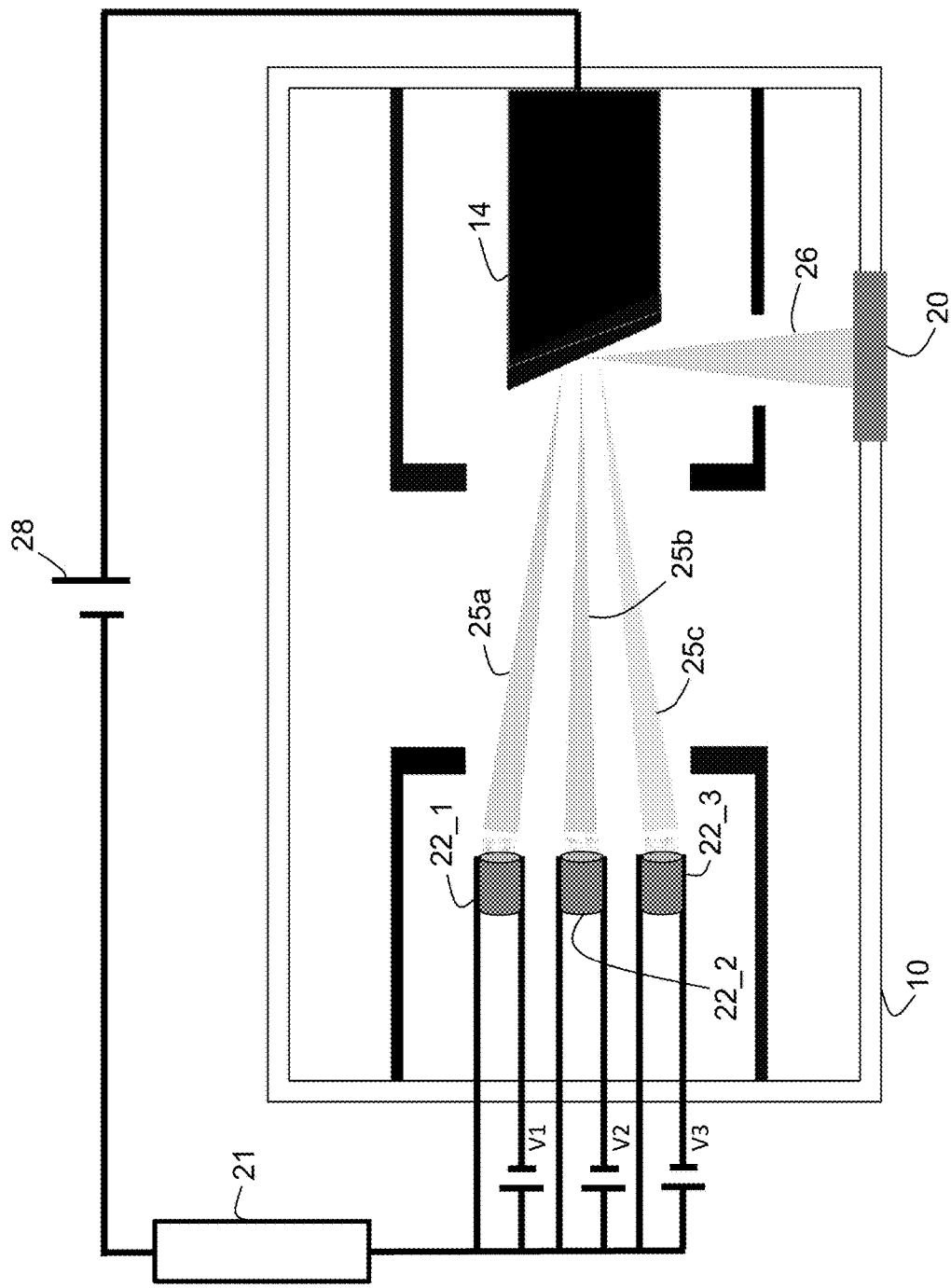
FIG. 5 is a schematic of an x-ray device comprising multiple electron emitters, according to some of the example embodiments described herein.

Thus, the coating increases the output intensity of electrons from the electron emitter. Thus, the overall advantages of this kind of electron emitter as manifested in a triode X-ray tube, as illustrated in FIG. 5, are the independency of the electron beam on the anode, and the enhanced current output. Furthermore, the field established between the electron emitter and the grid determines the intensity of the electron beam. Again, the voltage difference between the electron emitter and the electron-receiving component 24 determines the energy of the x-ray beam.

Figure 4:
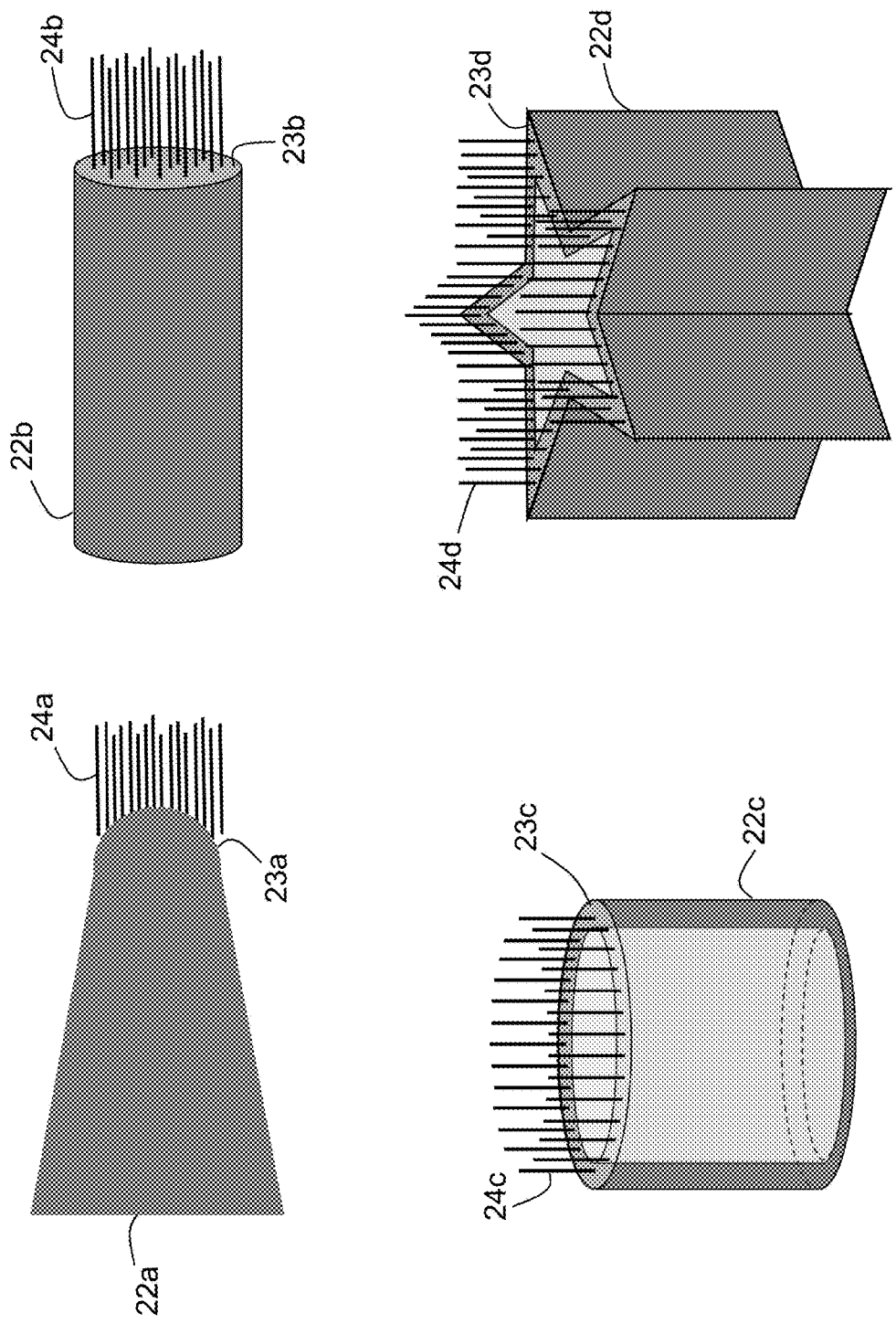
FIG. 4 is an illustrative example of different shapes an electron emitter may have, according to some of the example embodiments described herein.

FIG. 4 illustrates example shapes in which the electron emitter may be shaped. The electron emitter 22a is in the shape of a rounded pyramid comprising an electrically conductive substrate 23a and a coating of nanostructures 24a. A further example of an electron emitter 22b is provided in the form of a solid cylinder also comprising an electrically conductive substrate 23b and a coating of nanostructures 24b. FIG. 4 provides a further example of an electron emitter in the form of a hollow cylinder 22c featuring an electrically conductive substrate 23c and a coating of nanostructures 24c. An additional example of an electron emitter is provided in the form of a hollow star 22d comprising an electrically conductive substrate 23d and a coating of nanostructures 24d. It should be appreciated that such shapes may be adapted for different uses of the x-ray as the shapes may affect the direction of the emitted electrons. It should further be appreciated that other shapes may also be employed in the x-ray device according to the example embodiments.

According to some of the example embodiments, the nanostructure coating may be grown by a solid-liquid-gas phase method, chemical vapour deposition (CVD) process, or a chemical solution method. According to some of the example embodiments, the nanostructure coating is configured to be altered, with respect to morphology, to further facilitate the electron emission by chemical, electrochemical or optical means in or after the growth process.

According to some of the example embodiments, the nanostructure coating may be made of oxides, nitrides, silicides, selenides or tellurides. According to some of the example embodiments, the nanostructure coating may be made of oxide semiconductors, for example, ZnO. ZnO is an n-type, wide band gap semiconductor. The conductivity is associated with the oxygen vacancy generated in the growth process.

Improvement of the conductivity is achieved by doping the chemical elements in the columns IA, IIA, IB, IIIA, VIA, VIIA in the periodic table of the elements. Post-growth heat treatment is applied to homogenize the dopants or to partially segregate them to the surface. The morphology of the nanostructure can be altered by chemical or electrochemical means to achieve local field enhancement. UV treatment may also applied to improve the surface properties. A surface coating may be applied to the nanostructures to further enhance the electron emission process through decreasing the work function at the surface of the emitter. According to some of the example embodiments, a dielectric layer, for example, $SiO_2$, may be added on the electrically conductive substrate in areas in which the coating of the nanostructures is not present. Such a dielectric coating may be useful in directing the electron emission.

When a moderate heating is applied, via the heating element 21, while the electron emitter is negatively biased, the electrons are emitted by Schottky emission. When the heating is turned off, while the cathode is negatively biased, the electrons are emitted by field emission. The added function of heating, which is absent in current field emission x-ray sources, may also be applied to regenerate the electron emitter by removing unwanted adsorbed chemical species from the surface of the emitters in the case of cathode poisoning.

According to some of the example embodiments, multiple electron emitters may be used in the x-ray device. FIG. 5 illustrates an x-ray tube in which multiple electron emitters, in this embodiment, three electron emitters 22_1, 22_2 and 22_3, are assembled in the enclosed tube 10 with the emitters facing the electron-receiving component 14. The number and spacing of the electron emitters may vary.

It should be appreciated that any number of electron emitters may be employed in the x-ray device according to the example embodiments. It should further be appreciated that the electron emitters of FIG. 5 may be the electron emitter featured in any of FIGS. 2 thru 4, or an emitter of any other shape. It should also be appreciated that the electron emitters need not be identical and may comprise different shapes and/or characteristics with respect to one another.

The pattern of the arrangement of the electron emitters may be, but is not limited to, linear, rectangle, square, circular or hexagonal. With respect to the relation to the electron receiving component 14, the electron emitters 22_1, 22_2 and 22_3 may be arranged so that all of them emit electrons 25a-25c directed to one focal spot on the electron receiving component 14, or so that they project a magnified or demagnified image of the emission pattern onto the electron receiving component 14.

All these variations are intended to meet the requirement for the dimension and the shape of the x-ray beam 26. The electron emitters 22_1, 22_2 and 22_3 may be activated collectively or individually, simultaneously or sequentially. Such a flexible activation regime allows a high frequency, pulsing mode for x-ray generation by setting the output frequency of the power source, and a wide range of dose selection by choosing the number of activated electron emitters 22_1, 22_2 and 22_3. The activation of the electron emitters 22_1, 22_2 and 22_3 may be controlled by the power supply 28.

The example embodiments presented herein allow for the individual activation of the electron emitters 22_1, 22_2 and 22_3, thereby providing a mechanism for stabilizing emission current, which is not available in current x-ray systems. It should be appreciated that the inhomogeneity in the emission is a serious problem in large area cathodes or multi cathodes. This problem stems from the geometrical and physical inhomogeneity of the emitters.

In other words, the problem of the emitters described above stems from material and processing issues. Therefore, some of the example embodiments are directed towards an improvement on the growth of the emitter material on the substrate. According to some of the example embodiments, the existence of the inhomogeneity among the emitters is also solved at the component level. Such an example embodiment is described by taking a three-cathode configuration as example of FIG. 5.

Figures 6A, 6B:
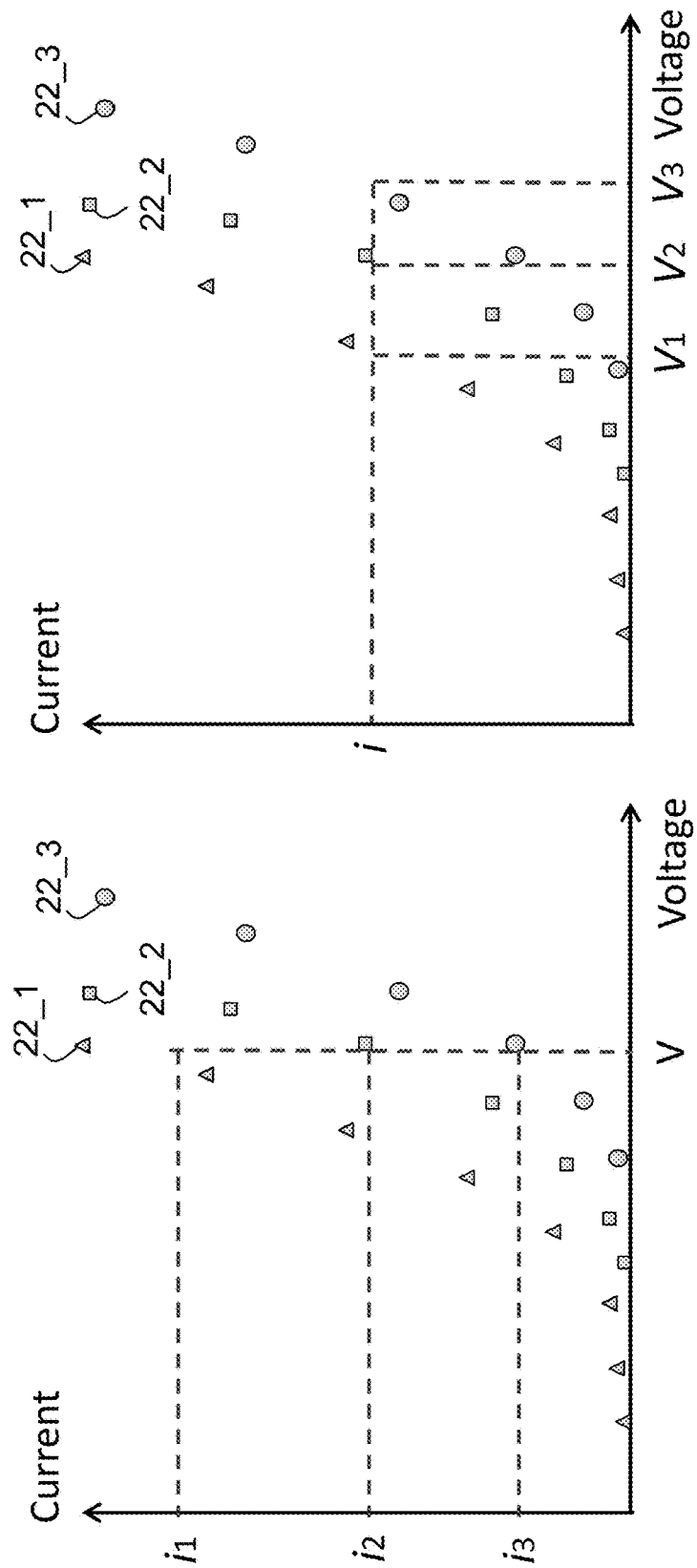
FIGS. 6A and 6B are graphs illustrating the I-V characteristics of the electron emitters of FIG. 5, according to some of the example embodiments described herein.
Figure 7:
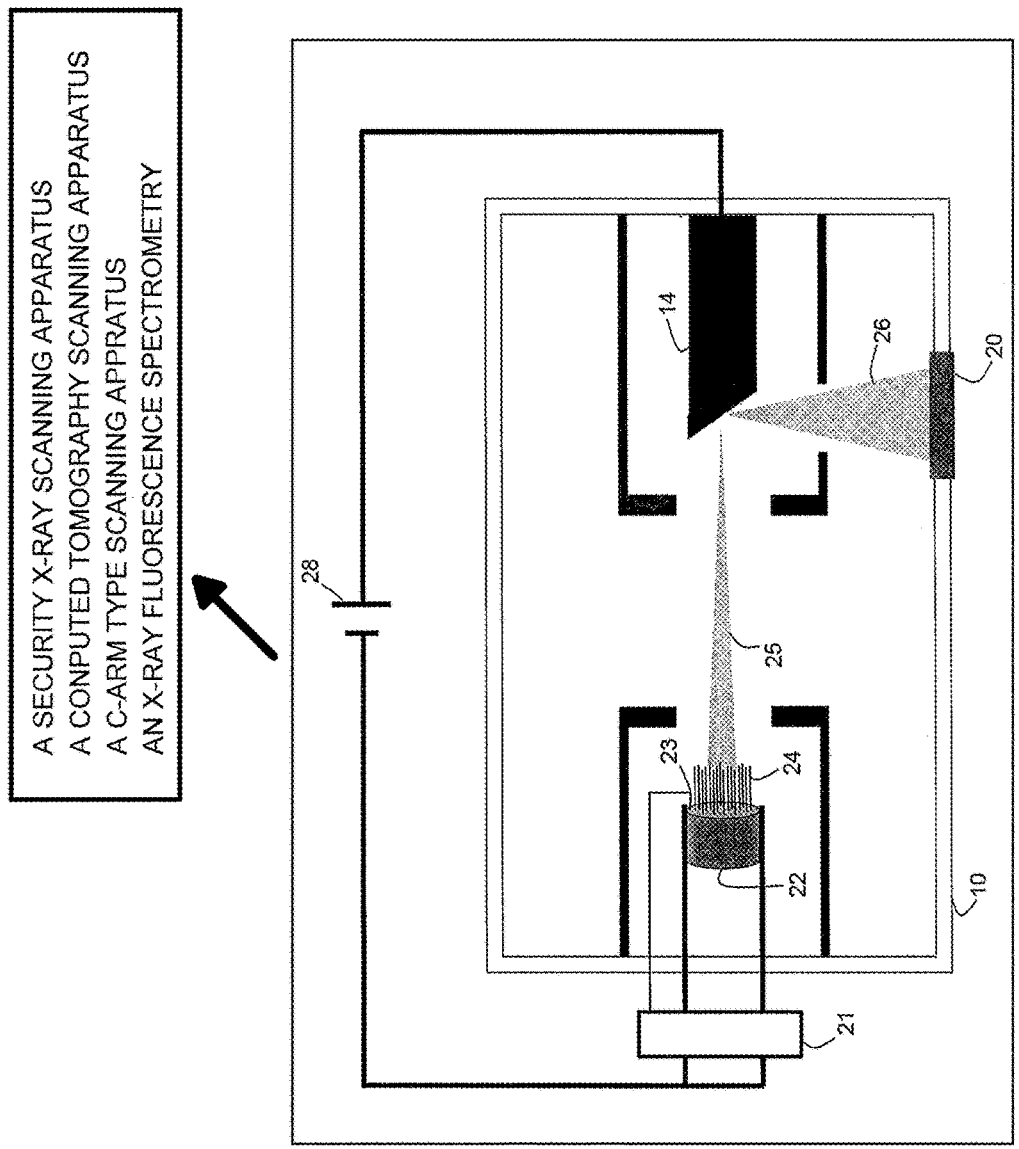
FIG. 7 illustrates example embodiments with a labeled representation.

FIGS. 6A and 6B illustrates the current and voltage characteristics of the electron emitter configuration of FIG. 5. In each graph, the plotted points represented by the triangular, square and circular plots represent electron emitter 22_1, 22_2 and 22_3, respectively, of FIG. 5.

FIG. 6A illustrates an application of voltage V, while keeping a same distance between the same electron emitter and electron-receiving component. Each electron emitter 22_1, 22_2 and 22_3, will emit current i1, i2 and i3, respectively. As shown in the graph of FIG. 6A, the amount of current supplied by the electron emission of each electron emitter differs. Although the inhomogeneity may be quantitatively described by formally defining the mean square error or root mean square deviation of the measured current values of all emitters in question, the graphical difference shown in FIG. 6A is sufficient to illustrate the point.

If all of the three electron emitters should emit the same current, then different voltages v1, v2, and v3 need to be applied to the electron emitters 22_1, 22_2 and 22_3, respectively, as seen in FIG. 6B. The advantageous consequence manifests itself when the electron emitters are directed to different focal spots to create a particular shape of the x-ray beam. The mechanism provides a spatial homogeneity of the x-ray beam by providing a constant current at all focal spots. A further advantage is that when the electron emitters are directed towards one focal spot, and biased sequentially, the emitters provide an electron emission with temporal homogeneity with a constant current over time. In addition, to ensure the stability and homogeneity of the x-ray emission, a feedback monitoring circuit may be used to control the electron emission process.

According to some of the example embodiments, the electrical power source 28 is further configured to supply a potential difference between the at least one electron generating component(s) and the electron receiving component for a diode tube in three bias modes, (−,0: cathode negative, anode grounded), (−,+: cathode negative, anode positive) and (0,+: cathode grounded, anode positive). The use of such bias modes is provided for inducing the Schottky emission. Thus, an example advantage of such an embodiment is the elimination of a cooling system or long cool down and warm up periods that are common for hot filament-based systems that utilize field emission. Thus, a more portable x-ray device may be obtained.

According to some of the example embodiments, the electrical power source is configured to operate in DC mode, i.e. constant (−, 0), (−, +), (0, +); pulse mode, i.e. square waves with anode grounded: or with the cathode grounded; or AC mode, i.e. a sinus wave An example advantage of providing an electrical power source with different modes of operations is the ability of providing a more versatile device. For example, in pulse and AC modes, a defined rising time, frequency, duty cycle and pulse shape of waveform may be obtained.

It should be appreciated that the x-ray device described herein may be used in a number of fields. For example, the x-ray device may be used in a security scanning apparatus, for example, as one would find in an airport security check. As the use of the heat element and the Schottky emission allows for a more portable device, the x-ray device may be easily implemented in such a security system.

A further example use of the x-ray device discussed herein is in medical scanning devices such as a computed tomography (CT) scanning apparatus or a C-arm type scanning apparatus, which may include a mini C-arm apparatus. A further example use of the x-ray device described herein is in a geological surveying apparatus.

It should be appreciated that the x-ray device described herein may be used in any non-destructive testing apparatus. A few example application of the x-ray device may be mammography, veterinary imaging, and X-ray fluorescence spectrometry, etc.

The descriptions of the example embodiments provided herein have been presented for purposes of illustration. The descriptions are not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatus, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

In the drawings and specification, there have been disclosed exemplary embodiments. However, many variations and modifications can be made to these embodiments. Accordingly, although specific terms are employed, they are used in a generic and descriptive sense only and not for purposes of limitation, the scope of the embodiments being defined by the following claims.

What is claimed is:

1. An x-ray generating device comprising:
   at least one electron emitter comprising an electrically conductive substrate, wherein the electrically conductive substrate comprises a coating of nanostructures;
   a heating element attached to each electrically conductive substrate of the at least one electron emitter;
   an electron receiving component configured to receive electrons emitted from the at least one electron emitter; and
   an evacuated enclosure configured to house the at least one electron emitter, the heating element and the electron receiving component;
   wherein the at least one electron emitter is configured for Schottky emission when the heating element is in an on-state and the at least one electron emitter is negatively biased,
   wherein a voltage difference between the electron emitter and the electron receiving component determines the energy of the x-ray beam.

2. The x-ray generating device of claim 1, wherein the at least one electron emitter is further configured for field emission when the heating element is in an off-state and the at least one electron emitter is negatively biased.

3. The x-ray generating device of claim 1, further comprising an electrical power source configured to control an operational state of the heating element.

4. The x-ray generating device of claim 3, wherein the electrical power source is further configured to supply a potential difference between the at least one electron generating component and the electron receiving component in three bias modes, (−,0: cathode negative, anode grounded), (−,+: cathode negative, anode positive) and (0,+: cathode grounded, anode positive).

5. The x-ray generating device of claim 3, wherein the electrical power source is configured to operate in DC mode, pulse mode or AC mode.

6. The x-ray generating device of claim 1, wherein the electrically conductive substrate is made of stainless steel, nickel, nickel based alloys, iron or iron based alloys.

7. The x-ray generating device of claim 1, wherein the nanostructures are doped or co-doped with a dopant element from column IA, IIA, IB, IIIA, VIA, or VIIA in periodic table of the elements.

8. The x-ray generating device of claim 1, wherein the nanostructures are made of ZnO.

9. The x-ray generating device of claim 1, wherein the electron receiving component is made of metal, a metallic alloy, a metallic compound, or a metal ceramic composite.

10. The x-ray generating device of claim 1, wherein the at least one electron emitter further comprises a grid situated at a fixed distance between 100 μm and 1000 μm via a spacer.

11. A security x-ray scanning apparatus comprising the x-ray generating device of claim 1.

12. A computed tomography scanning apparatus comprising the x-ray generating device of claim 1.

13. A C-arm type scanning apparatus comprising the x-ray generating device of claim 1.

14. A geological surveying apparatus comprising the x-ray generating device of claim 1.

15. An x-ray fluorescence spectrometry method comprising providing the x-ray generating device of claim 1.

* * * * *